United States Patent [19]

Collins

[11] Patent Number: 4,884,559
[45] Date of Patent: Dec. 5, 1989

[54] SURGICAL SPECULUM

[76] Inventor: Jason H. Collins, 1344 Covington Hwy., Slidell, La. 70460

[21] Appl. No.: 128,635

[22] Filed: Dec. 4, 1987

[51] Int. Cl.$^4$ ............................................... A61B 1/32
[52] U.S. Cl. ........................................ 128/17; 128/10; 128/345
[58] Field of Search ................... 128/17, 18, 9, 6, 345, 128/207.15, 303.14, 10, 11, 303, 315; 604/77, 21, 281

[56] References Cited

U.S. PATENT DOCUMENTS

| | | | |
|---|---|---|---|
| 2,243,285 | 5/1941 | Pope | 128/6 |
| 2,483,233 | 9/1949 | Pike et al. | 128/17 |
| 2,672,859 | 3/1954 | Jones | 128/17 |
| 3,037,505 | 6/1962 | Walden et al. | 128/3 |
| 3,830,225 | 8/1974 | Shinnick | 128/4 |
| 3,982,541 | 9/1976 | L'Esperance | 128/395 |
| 4,126,127 | 11/1978 | May | 128/16 |
| 4,596,564 | 6/1986 | Spetzler et al. | 604/281 |
| 4,632,108 | 12/1986 | Geil | 128/207.15 |
| 4,648,386 | 3/1987 | Morritt et al. | 128/4 |
| 4,735,603 | 4/1988 | Goodson et al. | 604/21 |

FOREIGN PATENT DOCUMENTS 578173  5/1923  France .

Primary Examiner—Edward M. Coven
Assistant Examiner—Mark S. Graham
Attorney, Agent, or Firm—Pravel, Gambrell, Hewitt, Kimball & Krieger

[57] ABSTRACT

The speculum includes a first top blade and second lower blade, the blades moveable in relation to one another via a rear hinge portion, as with a normal speculum. The lower blade of the speculum is further provided with a liquid evacuator tube extending along the interior of the speculum with an open protruding from the front of the blade for evacuating fluid from the patient during the laser surgery, and the top blade is provided with a second tube which is smoke evacuator tube similar to the liquid evacuator tube for evacuating smoke from the patient during laser surgery. In the preferred embodiment there is provided a trap in the handle portion of the speculum wherein the liquid evacuator tube and the smoke evacuator tube deposit any materials which are evacuated from the patient, the trap also including the third tube to a "stack house" filter which serves as the source for the suction created by the liquid evacuator and smoke evacuator tube.

4 Claims, 2 Drawing Sheets

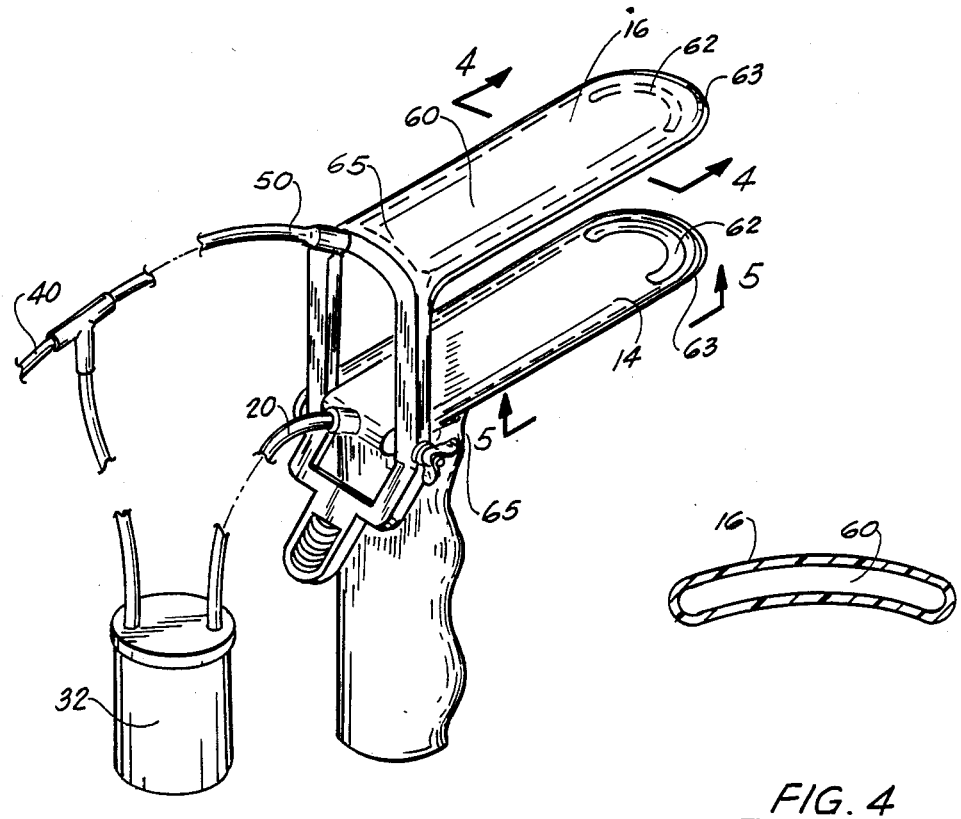
FIG. 3
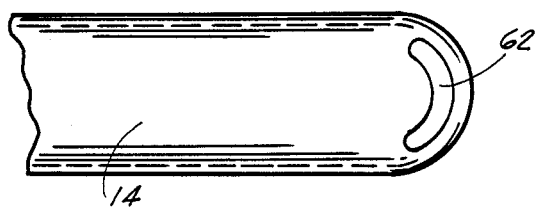
FIG. 4
FIG. 5

SURGICAL SPECULUM

BACKGROUND OF THE INVENTION

1. Field of the Invention

The apparatus of the present invention relates to a speculum. More particularly, the present invention relates to a speculum for drawing off excess fluid and smoke from a patient undergoing laser surgery in the treatment of cervical related disorders.

2. General Background

In the therapy and treatment of disorders of the cervix, there is a developing technique chosen for outpatient therapy which is safe, and produces adequate cure-aids and is relatively inexpensive. The vast majority of cervical intraepithelial neoplasia (CIN), lesions discovered in 80% of women screened for cervical cancer or early small lesions located on the exposed portion of the cervix, may be managed on an out-patient basis. Although cyrotherapy therapy is a state of the art technique in the treatment of such pathology, in recent years, the carbon dioxide laser has gained in popularity in both private and institutional practices. It has been claimed that laser therapy for CIN yields higher cure rates and faster healing than cyrotherapy in that the squamocolumnar junction retains its location at the external OS following treatment. In addition, therapeutic success in the art of 95% after a single treatment and 99% after two lasers treatments have been reported.

One of the concerns in the treatment of cervical condition through laser therapy is the problem surrounding the surgeons ability to properly perform laser surgery on the cervix due to the resultant stream of smoke that is emitted when the laser makes contact with human cells. This stream of smoke on one hand reduces a surgeon's ability to see properly the surgery being undertaken with the laser, and, on the other hand subjects the surgeon and surgical staff to cell fragments contained within the smoke or fluids which could be detrimental to the surgeon during such a technique.

As in all surgeries on the cervix, an instrument known as a speculum is utilized to increase the opening of the vagina so that the surgeon has relative easy access to the area being treated. In fact, there are known speculums which do contain a tube attached to the blade of a speculum for either blowing air upon or siphoning off smoke that may be a result of electrical conization or cauterization upon the cervix, in order to overcome the presence of smoke in the vagina. Several patents have been noted in the art, the most pertinent being as follows:

U.S. Pat. No. 2,483,233 issued to Price, et al, entitled "Speculum", relates to a speculum having a tube running in the upper jaw portion for blowing air into or for suctioning off smoke from the vagina following conization or cauterization upon the cervix.

U.S. Pat. No. 2,243,285, issued to Pope, entitled "Operating Scope", which is adapted for positioning of instruments therewithin, the scope adapted with a light source within the walls of the barrel for aspirating fluids therefrom.

U.S. Pat. No. 3,037,505, issued to Walden, entitled "Irrigators Or Spray Devices", relates to a spray device for distribution and injection of medication and cleaning preparations antibody cavities. The invention includes a spray tube which is readily detachable secured to a speculum but the second end of the tube may be coupled to a spring container.

U.S. Pat. No. 3,830,225, issued to Shinnick, entitled "Multi-Purpose Stop Cock Arrangement For Sucking Injection Oxygen Cessory Equipment", relates to a bronchoscope which allows the introduction or removal of fluid o instruments or both without withdrawing the other equipment from the bronchoscope.

Other art pertinent to the present invention is the Stack House Abdominal Smoke Control Valve which is a release system and valve that enables the laser surgeon to evacuate smoke from the inflated abdominal cavity during laser laparoscopy. The apparatus is manufactured and sold by Stack House Associates, Inc., which provides a filtration unit for the by-products from laser surgery of smoke and odor vaporized tissue through the use of a vacuum tube into the area of the laser. Such a filter would be used in conjunction with the present invention.

SUMMARY OF THE PRESENT INVENTION

The apparatus of the present invention relates to an improved speculum to be utilized in laser surgery. The speculum includes a first top blade and second lower blade, the blades movable in relation to one another via a rear hinge portion, as with a normal speculum. The lower blade of the speculum is further provided with a liquid evacuator tube extending along the interior of the speculum with an open protruding from the front of the blade for evacuating fluid from the patient during the laser surgery, and the top blade provided with a second smoke evacuator tube similar to the liquid evacuator tube for evacuating smoke from the patient during laser surgery. In the preferred embodiment there is provided a trap in the handle portion of the speculum wherein the liquid evacuator tube and the smoke evacuator tube deposit any materials which are evacuated from the patient, the trap also including the third tube to a "stack house" filter which serves as the source for the suction created by the liquid evacuator and smoke evacuator tube. In an additional embodiment, the passageway for the liquid evacuator is contained in a hollow passageway along the length of the body of the lower blade, and the smoke evacuator tube is comprised of a hollow portion along the length of the upper blade; both the smoke and fluid evacuator lines opening at their end portions on the front end of each of the top and lower blades respectively. In addition, the trap, which is contained in the hand of the preferred embodiment, may be positioned at a point away from the body of the speculum, but likewise having the same configuration, i.e., a third line leading to the "stack house" filter which is the source of the suction to evacuate the smoke and fluid from the patient's cavity during surgery. In the preferred embodiment, the speculum would be constructed of a plastic or the like disposable material that could be manufactured inexpensively and, therefore, may be discarded after a single use.

Therefore, it is a principal object of the present invention to provide a speculum particularly adapted for evacuating smoke and fluids from a patient undergoing laser surgery;

It is still a further principal object of the present invention to provide a surgical speculum which is adapted to evacuate smoke and fluid from a patient undergoing laser surgery and providing a trap housed within the body of the speculum for trapping particles evacuated therefrom prior to the evacuation of the smoke into a filter contained apart from the speculum;

It is still a further object of the present invention to provide a speculum for use in laser surgery where the smoke and fluid are evacuated from the patient through passageways contained within the body of the speculum therefore eliminating the need for separate tubes for the evacuation process;

It is still a further object of the present invention to provide a disposable speculum constructed of plastic or the like material.

BRIEF DESCRIPTION OF THE DRAWINGS

For a further understanding of the nature and objects of the present invention, reference should be had to the following detailed description, taken in conjunction with the accompanying drawings, in which like parts are given like reference numerals, and wherein:

FIG. 3 is an overall isometric view of an alternate embodiment of the apparatus of the present invention;

FIG. 4 is a cross-sectional view along lines 4—4 in FIG. 3 of the fluid flow bore incorporated into the body of the apparatus of the present invention; and FIG. 5 is a view along lines 5—5 in FIG. 3 of the fluid fluid flow bore in the alternate embodiment of the present invention.

DESCRIPTION OF THE PREFERRED EMBODIMENT

Figure 1:
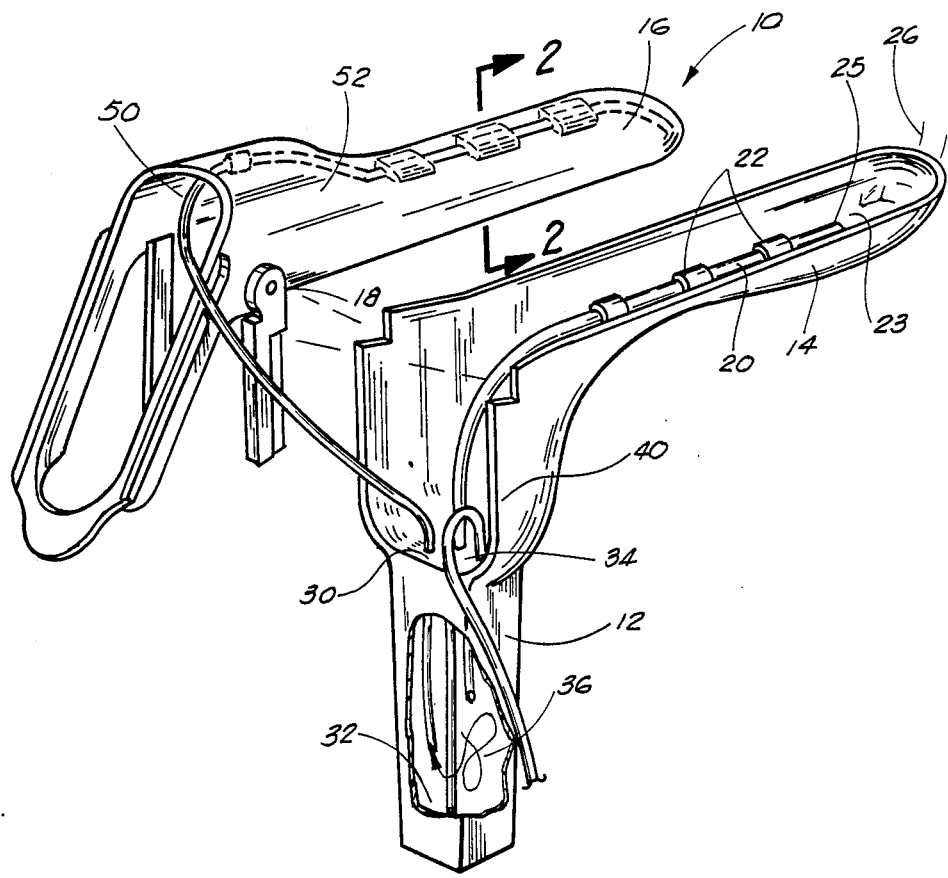
FIG. 1 is an overall isometric exploded view of the preferred embodiment of the apparatus of the present invention.
Figure 2:
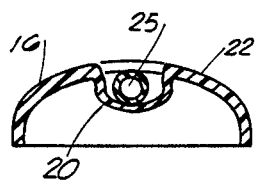
FIG. 2 is a cross-sectional view along lines 2—2 in FIG. 1 illustrating the fluid flow bore in the preferred embodiment of apparatus of the present invention.

The apparatus of the present invention is illustrated by the numeral 10 in the Figures. Improved speculum 10 is an improvement over the standard type of speculum which comprises a handle portion 12, a rigid lower jaw 14 integrally attached to handle portion 12, and a pivotally supported upper jaw 16 mounted upon a bearing pin 18 at the outer ends of handle portion 12 so that the upper jaw 16 is moveable between open and closed position in relation to the fixed jaw 14. In operation, the speculum is used in the normal manner and the jaw 16 is opened away from the fixed jaw 14 to hold the walls of the vagina properly dilated during laser surgery.

In the improved speculum as seen in the Figures, and of the preferred embodiment, speculum 10 would further include a liquid evacuator tube 20 housed within the confines of the lower jaw 14, with liquid evacuator tube 20 secured in place via a plurality of inserts 22 to secure liquid evacuator tube in position along the internal lower wall 23 of lower jaw 14, an evacuator tube opening up at its end portion 25 for evacuating fluid from the vagina therein as indicated by Arrows 26. The second end portion of liquid evacuator tube 20 extends downwardly along the lower wall 23 of lower jaw 14 into a means 30 for trapping any liquid and particles evacuated through tube 20 during the laser treatment. Means 30 includes a trap portion 32 contained within handle 12 having an upper wall portion 34 so that there is defined an area 36 contained within handle 12 for trapping the smoke and liquid therein. As seen in the Figures, there is an additional tube 40 extruding out from the top portion 34 of trap 32 which would lead to a filter unit known as a "stack house" filter, which provides the source for creating a suction within tube 40 for suctioning any liquid or smoke that is contained within trap 32 as will be discussed further.

Turning now to upper jaw 16, likewise, upper jaw 16 contains a smoke evacuator tube 50 again housed within the confines of the body portion of upper jaw 16 and secured along the upper face 52 of upper jaw 16 via a plurality of inserts 22. Smoke evacuator tube 50 likewise, leading into the upper wall 34 of trap 30 for evacuating smoke from the vagina through tube 50 into trap 32. Again, smoke like the liquid evacuated from the vagina, would be evacuated via a suction created by the "stack house" filter (not illustrated), which would operate in the same manner. For purposes of fluid capacity, in the preferred embodiment the trap would be sized to contain at least 50 cc of fluid during the process of laser treatment.

In an additional embodiment, as seen in FIGS. 3–5, the lower liquid evacuator tube 20 and smoke evacuator tube 50 may be eliminated along the length of the body portion of the lower jaw 14 and upper jaw 16 respectively, and in their place as is illustrated in FIG. 3, a hollow 60 would be cut into the body of the lower jaw 14 and upper jaw 16 along its length, the hollow ending in a arcuate opening 62 at the end portion 63 of blades 14 and 16 respectively, so that smoke and fluid may travel through the hollow to the back portion of the blades 14 and 16, wherein a tube such as tube 20 or 50 could be secured to the rear end 65 of the hollow for transmitting the fluid or smoke from the hollow into a trap 32 independent of handle portion 12 as seen in the Figures. Therefore, it would not be necessary to have a mean for securing the tube along the length of the body of blades 14 and 16, in view of the fact that the hollow would serve as the means for transmitting the fluid or smoke from the end of the speculum blades to the rear of the blades prior to the smoke or fluid traveling through the tubes into trap 32. In addition, in a particular embodiment as seen in FIG. 3, trap 32 is contained out of handle 12, and therefore would be secured independently of the speculum 10, so that tube 50, which would evacuate smoke via upper blade 16 would lead directly from the rear of hollow 60 into line 40 to the "stack house" filter. Likewise, tube 20 which is the liquid evacuator tube, would lead from the rear portion of lower hollow 60 into the trap 32 for depositing of any fluid or particles into trap 32 so that these could be trapped within trap 32 and would not be removed into the "stack house" filter.

However although FIG. 3 illustrates the trap 32 being located exterior to the handle portion of the apparatus, it should be noted that it is foreseen that the trap 32 may be contained within handle portion 12, so that the tubes 50 and 20 would lead directly from the blades 16 and 14 respectively, into ports and handle 12, directly into trap 32. This option, therefore, would allow the trap to be self-contained, and the apparatus operates as a single unit.

For purpose of construction, the laser speculum could be injection molded of plastic or the like so that the hollow 60 could be molded into the speculum when constructed and could be a disposable speculum that would be dispensed with after use. In addition, each hollow 60 would be provided with a means for quickly securing the end portion of tube 50 and 20 respectively onto blades 14 and 16, so that the speculum could be put into use very quickly and disposed of after use. In addition, the disposable laser speculum could be of various lengths and sizes, to fit various needs, and could be adjustable so that the speculum could be used in a variety of matters during laser surgery.

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A cervical speculum, comprising:
   (a) an upper blade member;
   (b) a lower blade member in substantial parallel relationship with the upper blade member;
   (c) a handle member;
   (d) means related to the handle member for moving said upper and lower blade members between open and closed positions relative to one another;
   (e) first and second tube means positioned in said upper and lower blade members respectively, the first tube means having a first end portion for evacuating smoke and the second tube means for evacuating fluid during cervical surgery while housed in said upper and lower blade members respectively; and
   (f) trap means positioned in the handle member for receiving said fluid and smoke evacuated during the cervical surgery.

2. The apparatus in claim 1, wherein the apparatus is constructed of a light weight disposable plastic material.

3. The apparatus in claim 1, wherein there is further provided suction means for receiving the smoke flowing into said trap member.

4. The apparatus in claim 1, wherein said trap member maintains the fluid evacuated through the tube in said upper blade member.

* * * * *